United States Patent [19]

Fraker

[11] Patent Number: 5,797,742

[45] Date of Patent: Aug. 25, 1998

[54] AMALGAM SOLIDS COLLECTING AND SEPARATING APPARATUS

[76] Inventor: Ross M. Fraker, 4510-54th Ave. N.E., Seattle, Wash. 98105

[21] Appl. No.: 610,145

[22] Filed: Feb. 29, 1996

[51] Int. Cl.[6] .................................................. A61C 17/04
[52] U.S. Cl. ........................... 433/92; 604/319; 209/173; 209/201; 210/515
[58] Field of Search ..................... 433/92, 95; 137/546; 209/158, 174, 194, 201, 185, 192, 173; 210/513, 515, 532.1; 604/319, 321

[56] References Cited

U.S. PATENT DOCUMENTS

| | | | |
|---|---|---|---|
| 568,145 | 8/1896 | Sanderson | 210/532.1 |
| 1,349,766 | 8/1920 | Hunt | 433/92 |
| 1,523,833 | 1/1925 | Olson | 209/201 |
| 1,617,254 | 2/1927 | Hurst, Jr. | 209/173 |
| 1,959,212 | 5/1934 | Miller | 209/158 |
| 3,035,959 | 5/1962 | Wang | 209/158 |
| 3,566,869 | 3/1971 | Crowson | 433/92 |
| 3,777,403 | 12/1973 | Ritchie | 433/92 |
| 3,845,765 | 11/1974 | Ikeda | 604/319 |
| 4,058,897 | 11/1977 | Edwards . | |
| 4,328,101 | 5/1982 | Broden | 210/320 |
| 4,360,428 | 11/1982 | Comparetto et al. | 210/188 |
| 4,385,891 | 5/1983 | Ligotti | 433/92 |
| 4,564,374 | 1/1986 | Hofmann | 55/57 |
| 4,643,197 | 2/1987 | Greene et al. | 604/319 |

FOREIGN PATENT DOCUMENTS

| | | | |
|---|---|---|---|
| 480881 | 4/1992 | European Pat. Off. | 433/92 |
| 3420278 | 12/1985 | Germany | 433/95 |
| 42498 | 12/1959 | Poland | 433/92 |
| 8302720 | 8/1983 | WIPO | 433/92 |

OTHER PUBLICATIONS

DRNA Amalgam Separator Product Brochure, undated.

*Primary Examiner*—Ralph A. Lewis
*Attorney, Agent, or Firm*—Seed and Berry LLP

[57] ABSTRACT

An amalgam solids collecting apparatus of the type for collecting an accumulation of a generally separable mixture of liquids and solids, including amalgam solids, and separating the solids from the liquids. The apparatus is connectable to a source of the mixture and is connectable to a vacuum source. The container has an interior area defining a collection portion therein and has an inlet port that communicates with the interior area of the container. The inlet port is couplable to the source of the mixture and the inlet port receives the mixture therethrough. The accumulation of the mixture is contained within the interior area with the headspace above the accumulation. The container has an outlet port with a second aperture therein that communicates with the interior area and that is located above the accumulation. An outflow tube extends through the outflow port, and the outflow tube has a first opening within the container and a second opening exterior of the container. The outflow tube is movable relative to the container between a raised position and a lowered position. In the raised position, the first opening is within the headspace above the accumulation of the mixture. In the lowered position, the first opening of the outflow tube is positioned within the accumulation and above solid particles that have settled from the accumulation to the bottom of the container. The outflow tube is connectable to a vacuum source to create a partial vacuum within the interior area of the container when the outflow tube is in the raised position and to withdraw the liquid from the container when the outflow tube is in the lowered position and when the solids are substantially separated from the liquid so the amalgam solids remain in the container.

24 Claims, 2 Drawing Sheets

5,797,742

AMALGAM SOLIDS COLLECTING AND SEPARATING APPARATUS

DESCRIPTION

1. Technical Field

The present invention is directed toward a dental apparatus, and more particularly, to a dental apparatus for collecting solid and liquid materials, drawn from the oral cavity of a patient, and separating the solid particles from the liquid, primarily for the purpose of permitting the recycling of the heavy metal components to prevent their entering a waste stream.

2. Background of the Invention

During conventional dental procedures, a mixture of solid and liquid material is removed from the oral cavity of a dental patient through a vacuum line connected to a vacuum system in the dentist's office. The solid material removed from the oral cavity typically includes amalgam containing silver, tin, copper, and mercury, or other precious metal particles from crowns and inlays, pieces of bone or ground tooth structure, gingival tissue, and food. In contrast, the liquid material typically includes water, saliva, blood, and pus or other infectious fluids. This mixture of solid and liquid material is drawn from the patient's mouth and transported in suspension to a waste stream. Treatment of the total mixture as waste, however, results not only in the loss of the amalgam and other precious metal particulates, hereafter collectively referred to simply as amalgam solids, but also could lead to heavy metal contamination of the earth or the sea. Since the amalgam solids provide relatively significant amounts of valuable material and are a possible source of pollution, separation of them from the liquid is highly desirable.

Various devices have previously been used in an attempt to separate the amalgam solids from the liquid. For example, the separator described in U.S. Pat. No. 4,385,891 attempts to separate the amalgam solids from the liquid as the mixture continuously flows through the apparatus on its way to a waste stream. Such conventional separators, however, have met with only limited success. This is primarily due to a relatively large percentage of amalgam solids remaining suspended in the liquid as the mixture passes through the apparatus. Thus, one of the main drawbacks of conventional separators is the inefficiency in the separation of the amalgam solids from the liquid, since often only the larger, heavier particles are trapped.

Accordingly, there is a need in this field for an apparatus capable of more fully separating the amalgam solids from the liquid, and which does not suffer from the problems associated with existing separators. The present invention fulfills this need, and provides further related advantages.

SUMMARY OF THE INVENTION

In brief, the present invention provides an apparatus that collects liquid and solid material, including the amalgam solids, removed from the oral cavity of a dental patient, and separates these amalgam solids from the liquid. In this manner, the amalgam solids may be further processed by known techniques to reclaim the valuable constituents therefrom and the environment is protected from potential pollution by heavy metals.

In a preferred embodiment of the present invention, the apparatus includes a container having an interior area and an inlet port with a first aperture therethrough that communicates with the interior area. The apparatus is connectable to a vacuum source, such as a that found in a dentist's office, and the inlet port is connectable to a vacuum line that carries a mixture of amalgam solids and liquid from the oral cavity to the container. The inlet port receives the suspended mixture from the vacuum line and directs it into the interior area such that an accumulation of this suspension is formed within the container and a headspace is provided above the accumulation. The suspension of the amalgam solids and the liquid is contained within the container until the amalgam solids settle to the bottom of the container, thus resulting in separation of the suspension into a residue layer of amalgam solids and a layer of liquid phase, known as the supernatant, above this residue.

In a further aspect of this embodiment, the container has an outlet port with a second aperture therein that communicates with the interior area. The outlet port is located above the accumulation of the mixture of amalgam solids and liquid. An outflow tube extends through the outflow port such that a first end of the outflow tube is within the container in the interior area and a second end of the outflow tube is exterior of the container. The outflow tube is movable relative to the container between a raised position, with the first end being in the headspace above the accumulation, and a lowered position, with the first end being within the accumulation. When the outflow tube is in the raised position and the vacuum system is activated, a partial vacuum is created in the container so as to draw the suspended mixture of liquid and amalgam solids through the vacuum line and into the container. When the supernatant is substantially separated from the amalgam solids, the outflow tube is moved to the lowered position with the second end being in the layer of supernatant above the amalgam solids, the vacuum system is activated, and the partial vacuum draws the supernatant out of the container, leaving the amalgam solids within in the container.

In a further preferred embodiment of the invention, the container has a body portion, a bottom portion connected to the body portion, and a top portion opposite the bottom portion. The inlet and outlet ports are in the top portion of the container. The top portion of the container is removably attached to the body portion of the container. The bottom portion of the container is removably attached to the body portion and is shaped and sized to retain the amalgam solids therein such that the amalgam solids remain in the bottom portion when the bottom portion is separated from the body portion of the container.

These and other aspects of this invention will become evident upon reference to the following detailed description and attached drawings.

DETAILED DESCRIPTION OF THE INVENTION

As mentioned above, the present invention is directed to an apparatus for collecting and separating an amalgam solids from a mixture of amalgam particles, other solids, and liquid removed from the oral cavity of a dental patient. The apparatus of this invention allows a dentist to collect the mixture over some period of time, such as one day, and then separate the supernatant from the solid material. The solid material, which contains the amalgam solids, may then be further processed by known techniques to remove the precious and potentially polluting constituents of amalgam solids. Substantial separation of the amalgam particles (and other solids) from the supernatant is achieved by allowing the mixture sufficient time, and by providing appropriate physical conditions to permit sedimentation of the amalgam particles and other solids. The supernatant is then drawn off the amalgam solids sediment, and the precious and potentially polluting constituents thereof are reclaimed.

Figures 1, 2:
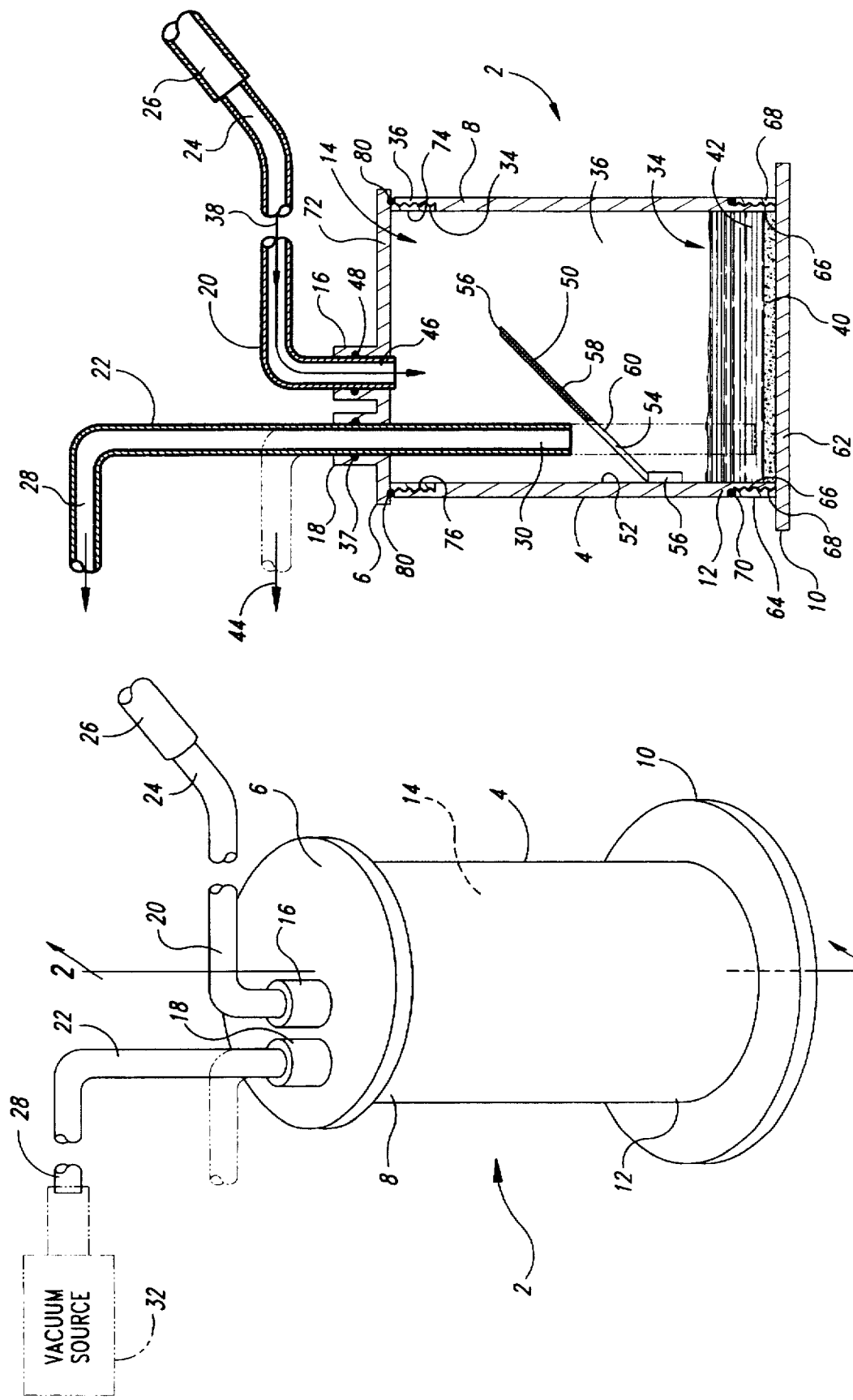
FIG. 1 is a top isometric view of a representative amalgam solids collecting and separating apparatus of the present invention with an outlet tube coupled to a vacuum source (shown in phantom lines), and with the outlet tube shown in solid lines in a raised position and in phantom lines in a lower position.
FIG. 2 is a cross-sectional view taken substantially along line 2—2 of FIG. 1 with supernatant and solids shown collected in a collection portion of the container.

A representative amalgam solids collector 2 in accordance with the present invention is shown in the figures for purposes of illustration. As best seen in FIGS. 1 and 2, the amalgam solids collector 2 includes a substantially cylindrical container body 4, a top 6 removably attached to an upper portion 8 of the container body, and a bottom 10 removably attached to a lower portion 12 of the container body opposite the top. The container body 4, the top 6, and the bottom 10 define an interior area 14 within the amalgam collector 2. The top 6 has an inlet port 16 and an outlet port 18 that extend therethrough and communicate with the interior area 14. An inlet tube 20 sealably passes through the inlet port 16 and into the interior area 14, and an outlet tube 22 slidably and sealably extends through the outlet port 18 and into the interior area.

The inlet tube 20 has an upper end portion 24 which is connected to a vacuum line 26 that conducts a mixture of amalgam solids and liquid from the oral cavity of a dental patient (not shown) through the inlet port 16 and into the interior area 14. The outlet tube 22 has an upper end 28 that is exterior of the container body 4 and a lower end 30 (FIG. 2) positioned within the interior area 14 of the collector 2. The outlet tube 22 is connected to a vacuum source 32, shown in phantom lines, that generates a suction force within the outlet tube to maintain a partial vacuum within the container body 4, thereby generating a suction force in the inlet tube 20 to draw the mixture of amalgam particles, other solids, and liquid from the oral cavity into the container body. As seen in FIG. 2, the mixture drawn into the collector 2 forms an accumulation 34 in the lower portion 12 of container body 4, leaving a headspace 36 between the accumulation and the top 6. In the preferred embodiment, the inlet and outlet tubes 20 and 22 have substantially the same cross-sectional area to maintain a generally consistent suction force within the vacuum line 26 and in the inlet and outlet tubes.

The outlet tube 22 is movable relative to the container body 4 between a raised position, shown in solid lines in FIGS. 1 and 2, and a lowered position, shown in phantom lines. An O-ring 37 is positioned in the outlet port 18 and sealably engages the outlet tube 22 to maintain the partial vacuum within the collector. During a dental procedure, the outlet tube 22 is in the raised position and the vacuum source 32 is activated to create a partial vacuum within the outlet tube, the container body 4, and the inlet tube 20. The partial vacuum draws the mixture of the amalgam particles, other solids, and the liquids from the patient's oral cavity through the inlet tube 20 and into the interior area 14 of the container body 4, as shown by arrow 38. In the raised position, the lower end 30 of the outlet tube 22 is positioned in the headspace 36 above the accumulation 34. Accordingly, the partial vacuum in the outlet tube 22 only draws air from the headspace 36 into the outlet tube and toward the vacuum source 32. The accumulation 34 is not drawn out of the collector 2 when the outlet tube 22 is in the raised position, so the mixture of amalgam particles, other solids, and liquid drawn through the inlet tube 20 is added to the accumulation and is retained in the collector.

In the preferred embodiment, the outlet tube 22 is maintained in the raised position for extended periods of time, such as during business hours of the dentist's office, so the mixture of amalgam particles, other solids, and liquid collected from one or more patients during the day is retained within the collector 2. The container body 4 has a volume of 1–5 gallons, such that a large quantity of the accumulation 34 may be collected from many dental patients over a selected period of time.

The accumulation 34 is retained in the collector 2, for an extended period of time, as an example, ten to twenty-four hours or longer, and the accumulation separates. The amalgam particles and other solids suspended or mixed in the liquid settle onto the bottom 10 of the collector 2 and form a lower amalgam solids layer 40 below an upper supernatant layer 42 containing primarily the liquid. After a sufficient time has passed to permit separation of the mixture, the outlet tube 22 is moved to the lowered position, as shown in phantom lines in FIG. 2. In the lowered position, the lower end 30 of the outlet tube 22 is positioned within the upper portion of the supernatant layer 42 above the lower amalgam solids layer 40. The partial vacuum in the outlet tube 22 draws the upper portion of the supernatant layer 42 out of the body 4 of the collector 2, thereby removing substantially only the supernatant through the outlet tube 22, as shown by arrow 44, while leaving the amalgam solids layer 40 substantially undisturbed in the bottom of the body 4 of the collector.

In the preferred embodiment, the outlet tube 22 is a generally rigid plastic tube that is manually moved between the raised and lowered positions. When the supernatant layer 42 is to be removed from the collector 2, a person grasps the outlet tube 22 and moves the outlet tube to the lowered position. When the collector 2 is to collect the mixture of amalgam particles, other solids, and liquid from a patient undergoing a dental procedure, the person grasps the outlet tube 22 and lifts it to the raised position before the dental procedure begins. In one embodiment, the collector 2 is sized to be stored generally adjacent to the chair and surrounding equipment used during the dental procedure. In an alternate embodiment, the collector 2 is stored in a remote location, such as a room separated from the area in which the dental procedures are conducted.

As best seen in FIG. 2, the inlet tube 20 has a lower end portion 46 that extends through the inlet port 16 and terminates in the headspace 36 above the accumulation 34. The mixture of amalgam particles, other solids, and liquid withdrawn from the patient flows through the inlet tube 20 and exits through the lower end portion 46 into the interior area 14 such that the mixture falls toward the accumulation 34. In the preferred embodiment, the inlet tube 20 is movable relative to the top 6 and the inlet port 16. An O-ring 48 is positioned in the inlet port 16, and the O-ring sealably engages the inlet tube 20 to maintain the partial vacuum within the collector 2.

The collector 2 includes a baffle 50 that is removably attached to an interior surface 52 of the container body 4 and positioned between the lower end portion 46 of the inlet tube 20 and the accumulation 34. The baffle 50 is positioned to receive the mixture of amalgam particles, other solids, liquid, and air stream from the inlet tube 20 as the mixture flows from the lower end portion 46 of the inlet tube 20. The baffle 50 interrupts the flow of the mixture and powerful airstream toward the accumulation 34 and partially redirects the flow of the mixture toward the interior surface 52 of the container body 4 so as to prevent the mixture from falling from the inlet tube's lower end portion 46 directly into the accumulation and greatly disperses the powerful air stream so as to prevent disturbance of the accumulation. Accordingly, the baffle 50 minimizes the disturbance and re-mixing of the separated or partially separated accumulation 34 in the collector 2 as additional amalgam particles, other solids, and liquid are added to the accumulation.

In the preferred embodiment, the baffle 50 has a pair of spaced-apart frame legs 54 that are removably attached at lower ends to brackets 56 connected to the interior surface 52 of the container body 4. The frame legs 54 extend inwardly away from the container body's interior surface 52 and upwardly toward the top 6, and the frame legs terminate at free ends 56 positioned in the headspace 34. A baffle screen 58 attached to the frame legs 54 spans between the frame legs directly below the inlet tube's lower end portion 50. The baffle screen 58 extends from the free ends 56 of the frame legs 54 toward the interior surface 52 of the container body 4 so as to redirect the mixture of amalgam particles, other solids, and liquid toward the interior surface 52 and to disperse the powerful air stream before the mixture is added to the accumulation 34.

The baffle 50 has a tube receiving area 60 therein between the frame legs 54 that is below the outlet port 18. The tube receiving area 60 is sized to movably receive a portion of the outlet tube 22 therethrough as the outlet tube is moved between the raised and lowered positions. In an alternate embodiment, not shown, the outlet port 18 is positioned away from the baffle 50 so the baffle is not directly below the outlet port and the outlet tube 22 does not extend through the baffle.

The baffle 50 is removable from the brackets 56 by lifting the frame legs 54 upwardly out of the brackets. In the preferred embodiment, the baffle 50 is removed for purposes of cleaning and maintenance, and the baffle is replaced in the brackets 56 before the collector 2 is used for a subsequent dental procedure.

As is best seen in FIG. 2, the bottom 10 of the collector 2 has a generally circular base plate 62 and an integral annular retention portion 64 projecting upwardly from the base plate. The annular retention portion 64 has a plurality of internal threads 66 thereon that removably and threadably engages mating external threads 68 in the lower portion of the container body 4. An O-ring 70 is attached to the container body 4 at the top of the external threads 68. The top of the annular retention portion 64 presses against the O-ring 70 when the bottom 10 is screwed onto the body portion 4 to an installed position so as to form a seal at the interface between the container body and the bottom. Accordingly, the O-ring 70 prevents any of the accumulation 34 from leaking from the collector 2.

The annular lower retention portion 64 of the bottom 10 projects a distance away from the base plate 62 such that the bottom of the container forms a cup-like structure that retains the amalgam particles and other solid material after the supernatant layer 42 has been removed from the collector 2. Accordingly, the bottom 10 is adapted to be unscrewed and removed from the body portion 4 and the amalgam particles and other solids in the bottom can be transported to a selected location and deposited for further processing and reclaiming of the amalgam solids. After the amalgam particles and other solids are removed from the bottom 10, the bottom is then reattached to container 4 for continued collection of amalgam solids and liquid mixture from dental patients.

As best seen in FIG. 2, the top 6 of the collector 2 has a generally circular top plate 72 with the inlet and outlet ports 16 and 18 projecting upwardly away from the top plate. An annular upper retention portion 74 is integrally attached to the top plate 72 and projects downwardly from the top plate and into the upper portion 8 of the container body 4. The upper retention portion 74 has a plurality of external threads 76 that removably engage mating internal threads 78 in the upper portion 8 of the container body 4. Accordingly, the top 6 is removable from the container body 4 by unscrewing the top relative to the container body and lifting the top away to provide access to the interior area 14 and to the baffle 50. An upper O-ring 80 is attached to the upper retention portion 74 adjacent to the top plate 72. The O-ring 80 presses against the upper edge of the container body 4 when the top 6 is in an installed position, and the O-ring forms a seal at the interface between top plate 72 and the container body 4. Accordingly, the upper O-ring 80 facilitates in maintaining the partial vacuum within the collector 2.

Figure 3:
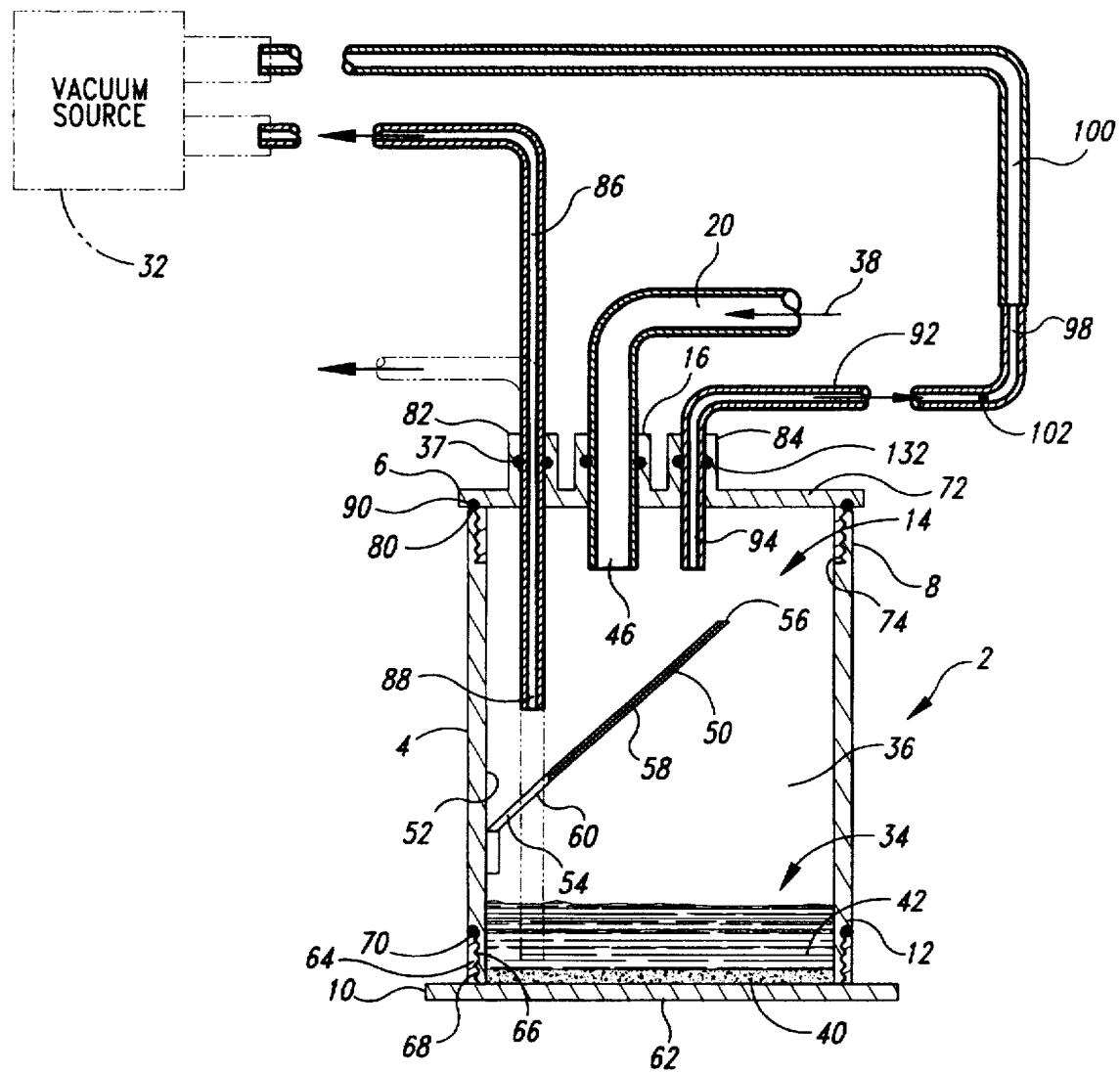
FIG. 3 is a cross-sectional view of an alternate embodiment of the present invention showing two outlet tubes extending through a top portion of the container and a single inlet tube adjacent to the outlet tubes.

In an alternate embodiment of the present invention shown in FIG. 3, the inlet port 16 extends through the top 6, and the first and second outlet ports 82 and 84 adjacent to the inlet port extend through the top to the interior area 14. The first outlet port 82 is positioned above the tube receiving area 60 in the baffle 50. A movable outlet tube 86 extends through the first outlet port 82 and is movable between the raised and lowered positions as discussed above, such that a lower end 88 is movable between the headspace 36 and the supernatant layer 42 of the accumulation 34. An O-ring 90 is positioned in the first outlet port 82 and sealably engages the movable outlet tube 86 to prevent loss of the partial vacuum within the collector 2 during operation.

A second, substantially fixed outlet tube 92 extends through the second outlet port 84 and terminates at a lower end 94 positioned within the headspace 36. An O-ring 132 is positioned within the second outlet port 84, and the O-ring sealably engages the fixed outlet tube 92 to avoid loss of the partial vacuum within the collector 2 during operation. The fixed outlet tube 92 has an upper end 98 removably connected to a vacuum line 100 that is connected to the vacuum source 32.

Each of the movable and fixed outlet tubes 86 and 92 have a cross-sectional area that is smaller than the cross-sectional area of the inlet tube 20. However, the movable and fixed outlet tubes 86 and 92 are sized so the combination of the cross-sectional areas is approximately equal to the inlet tube's cross-sectional area so as to maintain air flow through the tubes and to maintain the partial vacuum within the collector 2.

The fixed outlet tube 92 has an adjustable valve 102 between the second outlet port 84 and the tube's upper end 98. The valve 102 is movable between an open position and a closed position. When the movable outlet tube 84 is in the raised position and a partial vacuum is generated within the container body 4, the valve 102 is substantially open. The position of the valve 102 between the open and closed positions is adjusted to provide a selected partial vacuum in the container body 4 and a selected suction force in the outlet tube 92, such that the valve allows for accurate control of the removal of the supernatant layer 42 after the outlet tube 84 has been lowered into the supernatant.

The valve 102 is moved to the closed position when the movable outlet tube 84 is moved to the lowered position and into the supernatant layer 42 to maximize the suction within the movable outlet tube for removal of the supernatant layer from the container. In the preferred embodiment, the valve 102 is a petcock valve that is manually adjustable. The valve 102 provides for increased control of the partial vacuum within the collector 2.

From the foregoing, it will be appreciated that, although embodiments of the invention have been described herein for purposes of illustration, various modifications may be made without deviating from the spirit and scope of the invention. Accordingly, the invention is not limited except by the following claims.

I claim:

1. An amalgam solids collecting apparatus of the type used for collecting an accumulation of a generally separable mixture of liquid and solid particles that includes amalgam solids, the apparatus being connectable to a source of the mixture, and being connectable to a vacuum source, comprising:

a container having an interior area therein defining a collection portion within the container, the container having an inlet port that communicates with the interior area of the container, the inlet port being connectable to the source of the mixture and the inlet port being sized to receive the mixture therethrough to form the accumulation in the container with a headspace above the accumulation, the container having an outlet port with a second aperture therein that communicates with the interior area;

an outflow tube passing through the outflow port, the outflow tube having a first opening within the interior area and a second opening exterior of the container, the outflow tube being movable relative to the container between a raised position with the first opening being in the headspace and a lowered position with the first opening being within the accumulation, the second opening of the outflow tube being connectable to the vacuum source to create a partial vacuum within the interior area of the container when the outflow tube is in the raised position, and to withdraw the liquid from the container when the outflow tube is in the lowered position such that the amalgam solids remain in the container; and a second outflow port that communicates with the interior area wherein the second outflow port defines an outflow passageway between the interior area of the container and the exterior of the container, and a valve is coupled to the second outlet port by an outlet tube, the valve being movable between a closed position to close the outflow passageway and an open position to open the passageway.

2. The apparatus of claim 1 wherein the container has a body portion, a top attached to the body portion, and a bottom opposite the top, each of the inlet and outlet ports being in the top.

3. The apparatus of claim 2 wherein the top is removably attached to the body portion.

4. The apparatus of claim 2 wherein the bottom is removably attached to the body portion.

5. The apparatus of claim 4 wherein the bottom is shaped to retain the solid particles when the solid particles are substantially separated from the liquid.

6. The apparatus of claim 1, further including an O-ring seal in the outlet port, the O-ring seal sealably engaging the outflow tube.

7. The apparatus of claim 1, further including a baffle in the interior area of the container below the inlet port and positioned to be above the accumulation, the baffle being positioned to receive the mixture after the mixture passes through the inlet aperture and before the mixture enters the accumulation.

8. The apparatus of claim 1, further including an inflow tube extending through the inlet port, the inflow tube being connectable to the source of the mixture.

9. The apparatus of claim 8, further including an O-ring seal in the inlet port and sealably engaging the inflow tube.

10. The apparatus of claim 1 wherein the interior area of the container has a volume in the range of one gallon to five gallons.

11. A method of collecting and separating a mixture of solid particles and liquid from a patient undergoing an oral procedure, the mixture being an accumulation of the liquid and solid particles, a headspace being above the accumulation, comprising the steps of:

connecting a collecting container to a vacuum source, the container having an inlet port and an outlet port each communicating with the interior area, an inlet tube being connected to the inlet port and being couplable to the patient, the collecting container having an outlet tube movably extending through the outlet port, the outlet tube having a first end within the interior area and a second end exterior of the container, the second end being connected to the vacuum source, the outlet tube being movable relative to the outlet port between a raised position with the first end being in the headspace and a lowered position with the first end being within the liquid of the accumulation;

moving the outlet tube to the raised position;

activating the vacuum source to create a partial vacuum within the interior area when the outlet tube is in the raised position to create suction in the inlet tube;

drawing the mixture through the inlet tube and carrying the mixture to the container;

collecting the mixture in a bottom portion of the container to form the accumulation of liquid and solid particles when the outflow tube is in the raised position;

storing the accumulation in the container until the solid particles substantially separate from the liquid and the solid particles form a layer of solid particles in the bottom portion of the container and the liquid forms a layer of supernatant above the layer of solid particles;

moving the outlet tube to the lowered position after the solid particles have substantially separated from the liquid, the first end being positioned in the layer of supernatant and above the layer of solid particles; and drawing the supernatant through the outlet tube and removing the supernatant from the container and leaving the solid particles in the container.

12. The method of claim 11 wherein the container has a baffle within the interior area, and the method further including the step of passing the mixture over a baffle positioned in the container before the mixtures enter the accumulation.

13. The method of claim 11, further including removing the solid particles from the container after the supernatant has been removed.

14. The method of claim 11, further including moving the outlet tube to the raised position after the supernatant has been removed.

15. The method of claim 11 wherein the container has a second outlet port defining an outflow passageway between the interior area of the container and the exterior of the container, and a valve coupled to the second outlet port by an outlet tube, and the method further comprising the step of moving the valve to between a closed position to close the outflow passageway and an open position to open the outflow passageway to control a selected partial vacuum within the interior area of the container.

16. The method of claim 15 further comprising the step of moving the valve to the open position when the outflow tube is in the raised position.

17. The method of claim 15 further comprising the step of moving the valve to the closed position when the outflow tube is in the lowered position.

18. A method of collecting and separating a mixture of solid particles and liquid from a patient undergoing an oral procedure, the mixture being an accumulation of the liquid and solid particles, a headspace being above the accumulation, comprising the steps of:

connecting a collecting container to a vacuum source, the container having an inlet port and an outlet port each communicating with the interior area, a baffle within the interior area, an inlet tube being connected to the inlet port and being couplable to the patient, the collecting container having an outlet tube movably extending through the outlet port, the outlet tube having a first end within the interior area and a second end exterior of the container, the second end being connected to the vacuum source, the outlet tube being movable relative to the outlet port between a raised position and a lowered position;

moving the outlet tube to the raised position with the first end being in the headspace above the baffle;

activating the vacuum source to create a partial vacuum within the interior area when the outlet tube is in the raised position to create suction in the inlet tube;

drawing the mixture through the inlet tube and carrying the mixture to the container;

collecting the mixture in a bottom portion of the container to form the accumulation of liquid and solid particles when the outflow tube is in the raised position;

storing the accumulation in the container until the solid particles substantially separate from the liquid and the solid particles form a layer of solid particles in the bottom portion of the container and the liquid forms a layer of supernatant above the layer of solid particles;

moving the outlet tube to the lowered position after the solid particles have substantially separated from the liquid, the first end being positioned below the baffle and in the layer of supernatant and above the layer of solid particles; and drawing the supernatant through the outlet tube and removing the supernatant from the container and leaving the solid particles in the container.

19. The method of claim 18 further including the step of passing the mixture over the baffle before the mixtures enter the accumulation.

20. The method of claim 18, further including removing the solid particles from the container after the supernatant has been removed.

21. An amalgam solids collecting apparatus of the type used for collecting an accumulation of a generally separable mixture of liquid and solid particles that includes amalgam solids, the apparatus being connectable to a source of the mixture, and being connectable to a vacuum source, comprising:

a container having an interior area therein defining a collection portion within the container, the container having an inlet port that communicates with the interior area of the container, the inlet port being connectable to the source of the mixture and the inlet port being sized to receive the mixture therethrough to form the accumulation in the container with a headspace above the accumulation, the container having an outlet port with a second aperture therein that communicates with the interior area;

an outflow tube passing through the outflow port, the outflow tube having a first opening within the interior area and a second opening exterior of the container, the outflow tube being movable relative to the container between a raised position with the first opening being in the headspace and a lowered position with the first opening being within the accumulation, the second opening of the outflow tube being connectable to the vacuum source to create a partial vacuum within the interior area of the container when the outflow tube is in the raised position, and to withdraw the liquid from the container when the outflow tube is in the lowered position such that the amalgam solids remain in the container; and a baffle in the headspace within the interior area of the container below the inlet port and above the accumulation, the baffle being positioned to receive the mixture after the mixture passes through the inlet aperture and before the mixture enters the accumulation, the first opening of the outflow tube being in the headspace above the baffle when the outflow tube is in the raised position, and the first opening of the outflow tube being below the baffle when the outflow tube is in the lowered position.

22. The apparatus of claim 21 wherein the container has a body portion, a top removably attached to the body portion, and a bottom opposite the top, each of the inlet and outlet ports being in the top.

23. The apparatus of claim 21, further including an O-ring seal in the outlet port, the O-ring seal sealably engaging the outflow tube.

24. The apparatus of claim 21 wherein the container further includes a second outflow port that communicates with the interior area and that defines an outflow passageway between the interior area of the container and the exterior of the container, and a valve is coupled to the second outlet port by an outlet tube communicating with the outflow passageway, the valve being movable between a closed position to close the outflow passageway and an open position to open the passageway.

* * * * *